United States Patent [19]

Amotz et al.

[11] Patent Number: 4,572,897
[45] Date of Patent: Feb. 25, 1986

[54] CARRIER FOR IMMOBILIZING ENZYMES

[75] Inventors: Shmuel Amotz, Malov; Susanne Rugh, Rungsted Kyst; Erik K. Markussen, Vaerlose; Kurt Thomsen, Allerod, all of Denmark

[73] Assignee: Novo Industri A/S, Denmark

[21] Appl. No.: 539,305

[22] Filed: Oct. 5, 1983

[30] Foreign Application Priority Data

Oct. 6, 1982 [DK] Denmark ............................. 4430/82

[51] Int. Cl.$^4$ ...................... C12N 11/02; C12N 11/10; C12N 11/12; C12N 11/08
[52] U.S. Cl. .................................... 435/177; 435/178; 435/179; 435/180
[58] Field of Search ................................ 435/174–182

[56] References Cited

U.S. PATENT DOCUMENTS 4,106,991 8/1978 Markussen et al. .................. 435/187
4,110,164 8/1978 Sutthoff et al. .................. 435/182 X
4,116,771 9/1978 Amotz et al. ....................... 435/177
4,386,158 5/1983 Shimizu et al. .................. 435/178 X

FOREIGN PATENT DOCUMENTS 133380 5/1976 Denmark .
14003 8/1980 European Pat. Off. ............. 435/174
3336235 4/1984 Fed. Rep. of Germany ...... 435/174
1362365 8/1974 United Kingdom .

OTHER PUBLICATIONS

Derwent 08061 C/05 (1979).

Primary Examiner—Christine M. Nucker
Assistant Examiner—Shawn P. Foley
Attorney, Agent, or Firm—Fidelman, Wolffe & Waldron

[57] ABSTRACT

Immobilized enzyme granules prepared by mixing inert filler particles into an aqueous solution or dispersion of a water soluble binder, followed by granulating the mixture so as to form carrier granules. Enzyme is immobilized on the hydrophilic surfaces of the carrier granules. If not already insoluble in the medium for the intended enzymatic reaction, the binder in the granules is rendered insoluble, e.g., water insoluble.

Proteins are preferred binder materials, and glutaraldehyde is the preferred reagent for bonding enzyme to the carrier granules and for water insolubilizing the binder.

17 Claims, No Drawings

CARRIER FOR IMMOBILIZING ENZYMES

This invention relates to preparation of particulate form enzymes adapted for large scale use in packed bed or fluidized bed enzyme reactors. In particular, this invention pertains to enzymes immobilized by being bound at the surface of a carrier granule to the hydrophilic binder material thereof. In the carrier granule the binder material is in continuous phase; at least one particulate filler material is present as a discontinuous phase.

INTRODUCTION

It is believed by the inventors herein that the immobilized enzyme art is familiar with the physical properties desired for enzyme granules suited to large scale enzymatic conversions in fixed bed or fluidized bed columns. However, insofar as the inventors hereof are aware, the particulate forms of immobilized enzymes heretofore suggested to the art can be criticized for failure in one regard or another, be it for low compressive strength and/or hardness, low unit activity or simply inordinate material or manufacturing costs.

Thus, many workers in the art, besides Applicants, have appreciated that enzymes might well be placed on or in a carrier granule.

Usually the carrier has the form of small granules, possibly weighted, in which the enzyme is embedded, or on the surface of which the enzyme is attached or fixed. Reference is made to U.S. Pat. No. 4,266,029, U.S. Pat. No. 4,116,771 and Denmark Pat. No. 133,380, which are only three examples of carriers (on or in which enzymes are fixed) known in the art.

The carrier according to this invention belongs to the category of carriers, on the surface of which the enzyme is attached, in contradistinction to the category of carriers, in which the enzyme is distributed throughout the entire volume of the carrier.

A typical known carrier belonging to this category consists of granular gelatine and is described in Derwent 08061 C/5 (J5 4156-892). Particles of pure gelatine, however, are not hard enough for use in large scale fixed bed operations where very high flow rates are required. Also, particles of pure gelatine are relatively expensive.

A similar carrier granule also belonging to this category, whereby an inert core is coated by gelatine, can be produced according to U.S. Pat. No. 4,266,029. Though this carrier has good flow characteristics, it suffers from the disadvantage that the shape and size of the carrier granules cannot be chosen in accordance with the criteria for best performance in a column, but are predetermined by the particular sand fraction or other fraction of particulate dense material used as raw material. Furthermore, whereas it is easy to produce this carrier granule on a laboratory scale, it is difficult or perhaps impossible to manufacture on an industrial scale.

Another typical known carrier granule belonging to this category is described in Advances in Experimental Medicine and Biology, Vol. 42, Pp. 191-212, Immobilized Biochemicals and Affinity Chromatography. This carrier consists of glass beads with a silane coupling agent. These beads have excellent flow properties and relatively high loading capacity. However, they are very expensive, and like all inorganic carrier granules, to render them suitable for immobilizing enzymes, elaborate chemical treatment has to be performed, involving often the use of undesirable reagents.

Thus, an object of the invention is to immobilize enzymes on the surface of a carrier granule that exhibits sufficient hardness of column operations, a capability for production on an industrial scale, and low costs.

The disadvantages alluded to for the above referenced prior art immobilized enzyme carriers have been avoided in practice of this invention by creation of a composite carrier granule comprising a discontinuous phase of discrete, hard, inert (smaller) particles and a continuous phase of binder material. It should, however, be appreciated that not all such composite granules are within practice of this invention, and also that some comparable composite carrier granules have been suggested heretofore for immobilization of enzymes.

Immobilized glucose isomerase attached by ion exchange to a carrier granule containing a fibrous, ion exchange cellulosic incorporated in a hydrophobic polymer with a densification agent like powdered metal oxide being present is described in U.S. Pat. No. 4,110,164. The carrier is produced by mixing the cellulose and the densification agent into the melted polymer, then forming granules. Thereafter the enzyme is linked to the ion exchange cellulose.

Practice of this invention differs distinctly from the suggestions made by U.S. Pat. No. 4,110,164 in that Applicants link the enzyme to the continuous phase binder material. It so happens also that Applicants' binders themselves contrast sharply from binders suggested in U.S. Pat. No. 4,110,164 for being characterizable as hydrophilic polymers. The carrier granule of this invention can be described as a filled elastomer wherein the elastomer is a hydrophilic polymer insoluble in the medium for the intended enzymatic reaction. Since enzymatic reactions are commonly conducted in an aqueous medium, it is noted that preferably the hydrophilic polymer commences as a water soluble material, gelatine, for example, that becomes insolubilized during preparation of the immobilized enzyme granules.

THE INVENTION

The invention hereof comprises admixing filler particles with an aqueous solution or suspension of one or more water soluble binder substances. Then in an appropriate order, the resulting mixture is gelled, converted into granules, and the enzyme is bound to the hydrophilic binder material at the granule surface.

Except for instances when the enzymatic reaction for which the immobilized enzyme is intended will be carried out in a non-aqueous medium wherein the binder does not dissolve, a step necessary in practice of this invention is insolubilizing the water soluble binder by physical or chemical treatment, so that the continuous phase in the granules will not dissolve in the reaction medium.

As will be pointed out hereinafter, the order in which the suspension of filler particles in aqueous binder solution is converted into the granular enzyme products of this invention may be varied considerably.

For the sake of completeness it is noted here that the carrier granules may contain other components besides hydrophilic binder or binders and a filler, including, for example, granulating aids and more than one filler material, all such being contemplated within the sense of the term filler.

DISCUSSION OF THE INVENTION

The Filler

The filler material which forms a discontinuous phase in the carrier granule in then a multitude of discrete, hard and inert water insoluble particles that are inert to the binder, to the enzyme and to all ingredients in the enzymatic rection medium, including the medium itself. The term "inert" is intended herein to include in its sense, such attributes as insoluble and non-toxic.

Practice of this invention applies the wide knowledge and experience of the filled resin arts to preparation of a carrier for immobilized enzymes. Workers in the polymer arts have made detailed investigation into virtually every aspect of comparable composite materials formed into a continuous phase and a discontinuous phase. Articles from the filled resin arts abound in daily use as for example, paints which comprise pigments in a resinous matrix, tires which comprise carbon black particles in a rubber matrix with reinforcing cords therein as well, and (filled) thermoset articles (e.g., of urea-formaldehyde or phenol-formaldehyde). The body of knowledge relating to filled elastomers in particular, is applicable to practice of this invention. The entire range of water insoluble and inert fillers known to the filled elastomer arts are contemplated for filler purposes in the immobilized enzyme granules of this invention.

As might be expected, emphasis for selection of the filler materials employed in preferred practice of this invention is on their cost, i.e., least cost filler materials are generally preferred. Thus, the particulate filler in the carrier granule may well be diatomaceous earth, crushed sand, brick dust, clay, nylon powder, cellulose powder, metal oxides or metal salts, ground silica, aerosil, ground alumina, corundum, ground glass, ground flint, ground quartz, grond granite, aluminum phosphate, kaolin, bentonite, perlite, zeolites, calcium silicate, micro-cell filter-aid, crushed magnesium silicate, talc, asbestos, abraded hornblende, titanium dioxide, stannic oxide polishing powder, ground zirconium silicate, activated carbon, carbon black, bone meal, fly ash, metal fines. The filler may be any mixture of the above indicated materials. The materials listed above are cheap and give rise to carrier granules with good mechanical properties. However, some care is required regarding filler purity so as to avoid using a filler containing an impurity capable of releasing cations, albeit in small amounts, that the enzyme cannot tolerate. Such a filler would, of course, not be inert.

In the carrier granules, the amount of the discontinuous filler phase is between about 10 and about 98 weight %, in relation to the total weight of the carrier, preferably between 50 and 95 weight %, in relation to the total weight of the carrier.

A preferred shape for the carrier granule is spherical or rounded, with an average carrier diameter between 0.1 and 5 mm, preferably between 0.2 and 2 mm, between 0.2 and 1 mm being most preferred. In the above size range, a good compromise between flow properties and surface area is obtained. The filler particles are much smaller.

The linear size of the individual filler particles in the discontinuous phase, calculated as the diameter of a sphere with the same volume as a single particle, should be less than 1/5 of the smallest dimension of the carrier granule, which would be the diameter of a round granule, and preferably be less than 1/20 of the smallest dimension. Such particle sizes for the filler and smaller do not interfere with shaping of the carrier granules.

As is well understood by the filled elastomer arts, a great many physical properties of the finally shaped composite are determined largely by the filler including such properties as density, toughness and hardness (of the granule). Practice of this invention allows then the density, toughness, hardness of the carrier granule to be controlled principally through changes in filler material, filler particle size, filler loading, etc., which facilitates provision of high hardness, tough immobilized enzyme granules suited to large scale column operation at high flow rates.

That is not to say that toughness and hardness are not affected by the binder, but the significant degree of control over these properties through variation solely in the filler ingredient, allows binder selection and treatments thereof to be keyed correspondingly more towards the enzyme related characteristics of the granule. One direct result is that high unit activity hard, tough enzyme granules can be made according to practice of this invention far higher enzyme loadings for example, than can be obtained in the granules described by the aforementioned U.S. Pat. No. 4,110,164.

The Hydrophilic Binder

As already has been indicated, the hydrophilic binder material employed to form the immobilized enzyme granules of this invention must be capable of being dissolved in water, i.e, be water soluble. Some synthetic resins are characterized by water solubility, polyvinyl alcohol, and polyvinyl pyrrolidone, for example, and numerous cellulose derivatives, notably carboxy methyl cellulose, hydroxyethyl cellulose, hydroxypropyl cellulose, methyl cellulose and ethyl cellulose. Numerous naturally occurring polysaccharides are water soluble or can be solubilized, including notably agar, alginate, chitosan and starch. All of the above named materials, in particular, are well suited to practice of this invention. Proteins are the preferred binder materials, including notably gelatine, soy protein, albumen, zein, casein, gluten and protein hydrolysates (from fish meal, for example).

The Applicants hereof appreciate that many water soluble binder materials, including some listed above as being preferred are not particularly hard and tough. Some may not even be particularly good binders in their water soluble form. When a special immobilized enzyme granule is made, care in selection of the binder and the filler is advisable.

To a great extent, the physical properties of the binder material will depend upon the environment wherein the enzyme containing granule is employed. For instances in which the immobilized enzyme granules will be used is a non-aqueous medium, the (water soluble) binder may well be insoluble in the reaction medium. For example, if the immobilized enzyme is a lipase, and the lipase is intended to interesterify lipids in a petroleum ether solution, then albumen, casein, soy protein, hydroxyethylcellulose, agar, alginate, polyvinylalcohols, starch, methylcellulose or carboxymethylcellulose may be used as the hydrophilic binder without more since these materials are insoluble in petroleum ether. Moreover, only a loose attachment between the carrier granule and the enzyme is needed in this case.

For the most part, enzymatic reactions are carried out in aqueous medium necessitating conversion of the binder material into a water insoluble form. For example, if the enzyme on which the carrier granules eventually will be bound, is amyloglucosidase, and the amyloglucosidase is intended to split dextrins in aqueous solution, then it will be necessary to insolubilize the (originally) water soluble binder material. Usually, the amyloglucosidase would be fixed on the surface of the carrier granule by a crosslinking reaction, with glutaraldehyde for example.

The mode for insolubilizing the binder may be selected with a view toward improving hardness and toughness of the binder material and/or towards providing a substrate to which the enzyme binds well. For example, crosslinking proteins with glutaraldehyde generates a reasonable level of toughness and hardness in proteinaceous granules.

On the whole, the wide range of possible water soluble binders and the great range of possible fillers, together with the possibility for incorporating additional discontinuous phase ingredients, e.g., cellulose fibers for example, allows selections to be made for any individual enzymatic reaction that result in hard tough immobilized enzyme granules with high unit activity. As guide for such selection, the process variations hereinafter discussed and the preferred exemplary modes provided herein may be looked to.

Discussion of the Process

To repeat, the carrier granules herein contemplated are formed by dispersing the filler and any additional solid phase ingredients into an aqueous solution or dispersion of the water soluble binder or binders, then converting the mixture into granules and enzyme is immobilized on the granule surface bonded to the binder material. The carrier granule may be made porous or nonporous. In the latter event, the enzyme is immobilized on internal surfaces as well as on external surface of the granule.

As has been pointed out, the process might be without complication as when preparing an immobilized lipase to interesterify lipids in petroleum ether solution, for example. Then it is necessary only to granulate the mixture and thereafter wet the granules with an enzyme solution in a fluidized bed after which a final drying takes place.

However, when the enzymatic reaction will be carried out in aqueous medium, process considerations become more complex, since the binder must be insolubilized, and often the best product is obtained by bonding enzyme to the binder by chemical reaction, i.e., through co-valent bonds. The process sequence of this invention then includes insolubilization of the carrier granules and crosslinking of enzyme to the granule surfaces.

Considerable process variation is possible. A normal treatment sequence for the aqueous binder/filler mixture can be granulating, drying, insolubilizing, application of enzyme, crosslinking enzyme, then drying. However, insolubilizing and crosslinking may be conducted concurrently, or if separate, in either order. Sometimes, the liquid mixture may be gelled into a bead or granule form; then some or all of the drying step is deferred until after the enzyme has been crosslinked to the gel granules.

To illustrate the wide process variations available in practice of this invention description of different preferred process modes is offered herein for preparation of carrier granules made with some preferred binders, namely gelatine and alginate.

Mixtures of filler in binder solution or dispersion made with these binders may be gelled by extruding or dripping the mixture into a gelling medium whereby gel granules are formed. For the carbohydrate binders listed above, a solution containing $Ca^{++}$, $Ba^{++}$, $K^+$, polyphosphate, or ferricyanide are prefered gelling medium. For gelatine, cold water or a stream of cold air may be employed. In these modes of the invention, the binder (in the gel granules) is insolubilized, and enzyme is crosslinked to the binder material sequentially, in reverse order, or simultaneously.

According to one preferred mode of this invention, alginate and gelatine are both used. Dripping the mixture of filler in alginate/gelatine solution into a gelling medium, a $Ca^{++}$ solution, for example, converts the liquid mixture into alginate beads. Without need for drying, the beads are treated with a crosslinking reagent for the gelatine, preferably glutaraldehyde, thereby insolubilizing the gelatine, after which the alginate is dissolved and removed. Then, or before dissolving away the alginate, enzyme is incorporated on the beads, preferably by crosslinking with glutaraldehyde. The beads are not completely dried until processing into immobilized enzyme granules is otherwise completed.

Proteins, including notably gelatine, soy protein, cassein, albumin, zein, gluten and protein hydrolysate are particularly preferred for binder purposes. For insolubilizing of the protein in the carrier granule reaction with glutaraldehyde is particularly preferred. Also, crosslinking of enzyme to a protein binder by reaction with glutaraldehyde is particularly preferred.

Gelatine spheres or beads have been suggested heretofore, but prior art methods for their production known to Applicants are tedious and costly. Reference is made to Denmark Pat. No. 133,380 wherein is described production of such gelatine particles by addition of an aqueous solution of gelatine (and enzyme) to n-butanol and separation of the formed, drop-like particles. Practice of this invention according to the above-described method avoids need for solvent in the gelling medium.

It has been found also that spheres or rounded particles of a mixture of gelatine or other binder and the filler can be manufactured directly by means of a Marumerizer (vide e.g., U.S. Pat. No. 3,277,520) or by means of other granulating devices in particular, the system shown of U.S. Pat. No. 4,106,991. Furthermore, inclusion of the multitude of filler particles in the binder solution is believed to assist in the granulation.

In a preferred method according to the invention granule shaping is a spheronizing treatment carried out in a Marumerizer according to U.S. Pat. No. 3,277,520. In this manner, spheres with excellent physical properties suitable for column operation can be produced.

In another preferred method according to the invention the shaping is a spheronizing treatment carried out in a granulating device as described in U.S. Pat. No. 4,106,991. In this manner, very cheap spheres with excellent physical properties can be produced.

However, once the granules have been formed, they are insolubilized and enzyme is bound thereto. When a protein is the binder, e.g., gelatine, glutaraldehyde is the preferred reagent for both insolubilizing and enzyme crosslinking purposes. Then, carrier granules, crosslinking reagent, enzyme and any further agents may be brought together in any sequence with no particular sequence being more preferred.

In a preferred method according to the invention the granules are treated with an aqueous solution of the enzyme and with an aqueous solution of the crosslinking agent. Hereby a splendid adhesion between carrier and enzyme is obtained, and thus an immobilized enzyme granule, which has extremely good physical stability.

In a preferred method according to the invention the carrier granules are introduced into a tower as a fluidized mass and the solution of soluble enzyme is introduced into the tower as a spray, whereafter the thus produced mass is removed from the tower and treated wtih the crosslinking agent. Hereby the immobilized enzyme granules according to the invention can be produced with a very high loading of the enzyme on the carrier granules.

In a preferred method according to the invention, the carrier granules are introduced into a tower as a fluidized mass using air as the fluidizing gas and a solution containing both soluble enzyme and crosslinking agent is introduced into the tower as a spray, whereafter the thus produced mass is removed from the tower. Hereby the immobilized enzyme according to the invention can be produced with a very high loading of the enzyme on the carrier.

However prepared, the shape of the immobilized enzyme granule after drying is spherical or rounded, and the average granule diameter is between 0.1 and 5 mm, preferably between 0.2 and 2 mm. As has already been pointed out, this size range offers a good compromise between flow properties and surface area. This size range is convenient for using the immobilized enzyme granules to form the bed in fixed bed or fluidized bed columns.

The following Examples illustrate the method and products according to the invention. In some of the Examples, only the production of the carrier granule is described. For these Examples, it should be understood that the carrier granules were treated with the same enzyme solution described in Example 12 and further treated as described in Example 12, whereby immobilized enzyme granules were produced. In addition, production of the immobilized enzyme granules as exemplified herein, immobilize the enzyme according to practices disclosed in co-pending application, Ser. No. 539,303, filed concurrently herewith, since such practices form part of the best modes for practices of the invention hereof.

In some of the Examples, a value of the pressure drop (physical strength) during column operation is indicated. This value is determined in accordance with AF 166/2, which is a description of a laboratory procedure, a copy of which can be obtained from NOVO INDUSTRI A/S, Novo Alle, 2880 Bagsvaerd, Denmark. Some theoretical considerations connected to this pressure drop determination are described in Starch/Stärke 31 (1979), No. 1, Pp. 13-16. For comparison with known commercial products it may be mentioned that the best values of the pressure drop for the immobilized glucose isomerase preparations SWEETZYME ® is around 10 g/cm$^2$. It appears from the Examples that pressure drops with the carriers according to the invention can be as small as 2 g/cm$^2$ and that all values are considerably lower than 10 g/cm$^2$, whereby the technical advantage of the invention is clearly demonstrated.

EXAMPLE 1

10 g gelatine Bloom 260 were dispersed in 60 ml H$_2$O, 33 g of 6% w/v Na-alginate was added, the mixture was heated to 60° C. to dissolve the gelatine, then 10 g of Hyflo Celite (diatomaceous earth) was added, the whole mixture was stirred for 10 minutes at 55° C. and pumped through a vibrating syringe to produce very fine droplets, which were allowed to drop into a 2% w/v CaCl$_2$ 2H$_2$O solution, maintained at 5° C. The sphere-like particles thus produced were stirred in the CaCl solution for a few minutes, then removed from the solution, washed with de-ionized water and allowed to dry for 2 days at room temperature. The particles were then gently stirred for 1 hour in 200 ml 1% w/v glutaraldehyde solution at pH 8.5, removed, washed in de-ionized water, and again allowed to dry. In this way spherical and extremely hard and cohesive particles with a diameter of approximately 2 mm and exhibiting excellent flow properties were obtained. The pressure drop was 2 g/cm$^2$. The particles could be treated with citrate or phosphate, to remove the Ca$^{++}$ and the alginate, if so desired, without any ill effect to the particles.

EXAMPLE 2

The procedure described in example 1 was repeated, except that half the amount of gelatine, that is 5 g, and twice as much Hyflo Celite, that is 20 g, was used, and the particles were not allowed to dry before being treated with glutaraldehyde. Essentially identical particles were thus obtained, with somewhat reduced hardness, yet with almost the same excellent flow properties. The pressure drop was 3 g/cm$^2$.

EXAMPLE 3

The procedure described in example 2 was repeated, except that gelatine Bloom 200 was used, and the amount thereof reduced to 4 g. The concentration of glutaraldehyde was also reduced to 0.2% w/v. Particles with essentially identical properties were obtained in this manner.

EXAMPLE 4

In this example pilot-plant equipment was used. Thus, 0.7 kg cellulose fiber, type Arbocel BC 200, 2.8 kg Clarcel Celite (diatomaceous earth) and 4 kg 20% w/w gelatine Bloom 200 solution, all at 60° C., were mixed in a plow-share mixer of the type Lödige FM 130 D, and the thick mass so obtained was extruded by an extruder equipped with a 1.5 mm screen and then spheronized in a Marumerizer ®, as described in U.S. Pat. No. 3 277 520. The extruder was of the twin screw type model EXDC-100, and the spheronizer model was Q-400. The particles thus obtained were dried in a fluid-bed tower (Glatt type WSG 15) and sieved, and the fraction 1.2-2.0 mm collected, with the residue recycled. A sample of 10 g was then treated for 3 hours at room temperature with 100 ml 1% w/v glutaraldehyde solution adjusted to pH 7.0, removed from the solution, and thoroughly washed with de-ionized water. Even without drying the thus obtained particles were extremely hard and cohesive and with excellent flow properties. The pressure drop was 2 g/cm$^2$. In this example the discontinuous phase constituted 65% by weight of the particle.

EXAMPLE 5

In this example the same Marumerizer was used as in example 4, except that no extruder was used. Furthermore, the contents of the discontinuous phase was raised to 94% w/w of the total weight of the carrier. Thus, 1.5 kg Skamol clay particles with a particle size of 0.7–1.0 mm were loaded into the spheronizer, and 0.4 kg Hyflo Celite and 1.15 kg 10% w/w gelatine Bloom 80 solution at 60° C. were added alternately, so as to avoid formation of lumps. The particles thus obtained were treated as in example 4, whereby very hard particles with very good flow properties were generated. The pressure drop was 5 g/cm$^2$.

EXAMPLE 6

In this example a granulator of a plow share type mixer, Lödige FM 50, equipped with a high-speed chopper as described in U.S. Pat. No. 4 106 991, was loaded with 5.0 kg Clarcel Celite, and 5.95 kg 16% w/w gelatine Bloom 200 was sprayed into it, whereby the treatment time and the rotation speeds of the mixer and the chopper were chosen in such a manner that a particle size of 0.7–1.5 mm was generated. These particles were treated as in example 4, whereby carrier particles with essentially the same properties as in example 4 were generated. The pressure drop was 4 g/cm$^2$.

EXAMPLE 7

1 kg cellulose fiber, 4 kg Clarcel Celite and 10 kg of recirculated material produced according to this example were sprayed with 10.5 kg 10% w/w gelatine Bloom 200 in a plow share Lödige mixer type FM 130 D, whereby rounded particles of varying size were generated. During all the previously described operations both ingredients and equipment were maintained at 55° C. The rounded particles were dried in a fluid-bed tower and sieved, and the fraction 0.5–0.7 mm comprising 32% was collected. The residue comprising coarser particles which were milled, and fines which were used directly, was recycled, as described in the beginning of this example.

EXAMPLE 8

The same mixer as in example 4, i.e. Lödige FM 130 D, was loaded with 3 kg cellulose fiber, 10.5 kg Clarcel Celite and 1.5 kg albumen at ambient temperature and sprayed with 15.2 kg water. The treatment time and rotation speeds of the mixer and the chopper was chosen in such manner, that particles of the preferred size were generated. The particles were dried in a fluid bed and a sieve analysis on the dried particles showed the following particle size distribution:

| >1000 | μm | 19.7% |
|---|---|---|
| >850 | " | 35.6% |
| >707 | " | 58.8% |
| >600 | " | 78.2% |
| >500 | " | 92.1% |
| <420 | " | 1.1% |

EXAMPLE 9

The procedure in example 8 was repeated, except that 1.5 kg isoelectric soluble soy protein hydrolyzate was substituted for the albumen and that the amount of water was 14.8 kg. Sieve analysis on the dried particles showed the following particle size distribution:

| >1000 | μm | 24.2% |
|---|---|---|
| >850 | " | 43.2% |
| >707 | " | 66.1% |
| >600 | " | 84.4% |
| >500 | " | 95.2% |
| <420 | " | 1.0% |

EXAMPLE 10

The same mixer as in example 6, i.e. Lödige FM 50, was loaded with 11.3 kg Al$_2$O$_3$ and 3.0 kg cellulose fiber and sprayed with 650 g Gelatine Bloom 200 in 4.55 kg water. The temperature was kept at 55° C. The particles formed by the rotation of the mixer and the chopper was dried in a fluid bed. Sieve analysis showed the following particle size distribution:

| >1000 | μm | 8.5% |
|---|---|---|
| >850 | " | 16.1% |
| >707 | " | 31.2% |
| >600 | " | 46.2% |
| >500 | " | 65.3% |
| <420 | " | 15.6% |

EXAMPLE 11

The Lödige FM 130 D mixer was loaded with 2.1 kg cellulose fiber, 8.4 kg Clarcel Celite and 4.5 kg sodium chloride and sprayed with 11.0 kg 10% (w/w) gelatine Bloom 80. The temperature was 55° C. The particles were formed and dried. Sieve analysis showed the following particle size distribution:

| >1000 | μm | 14.2% |
|---|---|---|
| >850 | " | 23.7% |
| >707 | " | 40.1% |
| >600 | " | 59.1% |
| >500 | " | 79.1% |
| <420 | " | 5.8% |

EXAMPLE 12

This example describes a method for production of an immobilized enzyme preparation according to the invention. Thus, 4.5 kg of carrier particles produced as in example 4 treated with glutaraldehyde, washed and dried were fluidized in a pilot-plant fluid bed apparatus (Glatt type WSG 15), and 9.3 kg solution of 19% w/w partly purified glucose isomerase from Bacillus coagulans NRRL 5650 (activity 3240 units/g dry matter, the activity unit being defined in NOVO analyseforskrift AF 189/1), was sprayed onto the particles at 50°–55° C., and the particles were allowed to dry. The product thus obtained contained 28% by weight of partly purified glucose isomerase, with 85% enzyme activity recovery. 20 g of these particles were then treated in 500 ml solution containing 0.06M NaH$_2$PO$_4$.2H$_2$O, 1.4M Na$_2$SO$_4$, and 0.1% w/v glutaraldehyde, adjusted to pH 7.0 with 1N NaOH. After 1 hour at room temperature the particles were removed and washed thoroughly with 0.06M sodium phosphate of pH 7.0 and then superficially with de-ionized water, and part of them were allowed to dry. Both the wet and the dried particles showed the same excellent flow properties as the original carrier, and no leakage of activity could be detected. However, in the wet particles the enzyme activity recovery was 70%, while in the dried particles it was only 48%.

EXAMPLE 13

20 g of dried carrier particles produced as in example 4 were fluidized in a Lab type fluid bed. 45.8 g of 11.0% w/w homogenized cell sludge (fermented as indicated in example 1 of Danish patent application No. 5190/79, sludge produced as indicated in example 4 of Danish patent application No. 5190/79) containing 80.1 U/g of thermophilic lactase from Bacillus sp. NRRL B-11.229 were sprayed onto the carrier particles at 30°-40° C., and the coated particles were allowed to dry. The lactase activity unit is defined as that amount of lactase, which will split 1 μmol of lactose/minute under the following reaction conditions: Substrate concentration=10% lactose, temperature=60° C., pH=6.5 and reaction time=30 minutes. The enzyme activity recovery was 79.8%. 10 g coated spheres were then treated in 250 ml solution containing 0.06M $Na_2HPO_4$, 1.4M $Na_2SO_4$ and 0.1% w/v glutaraldehyde at pH 7.5. After 1 hour at room temperature the particles were removed and washed thoroughly with 0.06M $K_2HPO_4$ at pH=7.5. The enzyme activity recovery in regard to the crosslinking step was 17.2%.

EXAMPLE 14

24 g of dried carrier particles produced as in example 4 were soaked in 20.2 g solution of a 39.6% w/w partly purified amyloglucosidase from A. niger produced by ultrafiltration of the commercial product AMG 200 L (described in NOVO brochure AMG, B 020 g—GB 2500 July 1982) in order to remove low molecular constituents to a dry matter content of 39.6% w/w (activity 2610 IAG/g, the activity unit being defined in NOVO Analyseforskrift AF 159/2). Vacuum was applied for 1 hour. The product thus obtained contained 25% by weight of enzyme dry matter with 77.9% enzyme activity recovery.

20 g particles with 71.8% dry matter were then treated in 1600 ml of a solution of 1% w/v $NaH_2PO_4$, 20% w/v $Na_2SO_4$ and 0.2% glutaraldehyde at pH=4.5. After 1 hour the particles were removed by filtration and washed with 1% $NaH_2PO_4$ at pH=4.5.

The enzyme activity recovery in regard to the crosslinking step was 55.1%.

EXAMPLE 15

40 g carrier particles prepared as indicated in example 4 and with a dry substance content of 98.8% and 24 g vacuum evaporated partially purified Bacillus coagulans glucose isomerase (NRRL 5650) concentrate with 5% glucose and 8% sodium sulphate added (dry substance 41.8%) was mixed and the liquid was allowed to displace the air in the pores of the particles by vacuum treatment. Weight after mixing was 63.22 g. Dry substance was 79.2%.

18 g portions of this preparation (14 g dry substance) were treated for 1 hour at room temperature with 375 ml of a solution containing in all cases 22% sodium sulphate, 5% glucose, and 1% sodium phosphate, adjusted to pH 7.5, and furthermore either 0.1, or 0.2 or 0.3% glutaraldehyde.

After this treatment the preparations were washed five times with approx. 150 ml % sodium phosphate, pH 7.5.

The enzyme activity was determined according to AF 189/1 after draining of the liquid from the particles. Also dry substance was determined on the drained particles.

| | % dry substance | U/g wet | U/g dry | Yield, % | Immob. yield, % |
|---|---|---|---|---|---|
| Enzyme concentrate | 41.8 | 1415 | 3385 | — | — |
| Enzyme concentrate + carrier | 79.2 | 463 | 585 | 86 | — |
| Immob. with 0.1% GA | 32.5 | 158 | 486 | 72 | 83 |
| Immob. with 0.2% GA | 38.9 | 141 | 362 | 53 | 62 |
| Immob. with 0.3% GA | — | 117 | 333 | 49 | 57 |

Portions equivalent to 5 g dry substance were tested for pressure drop.

| Glutaraldehyde concentration at immobilization | Pressure drop | |
|---|---|---|
| | 25 hours | 50 hours |
| 0.1% | 3 | 5 |
| 0.2% | 1 | 3 |
| 0.3% | 2 | 3 |

EXAMPLE 16

The same mixer as in example 4, i.e. Lödige FM 130 D, was loaded with 3 kg cellulose fiber and 13.5 kg Clarcel Celite and sprayed with 15 kg 10% w/v polyethyleneimine PEI 15 T, Taihei Sangyo Kaisha Ltd., at ambient temperature, thereafter with 3.0 kg water and finally with 2 kg 50% w/v glutaraldehyde. The treatment time and rotation speeds of the mixer and the chopper was chosen in such manner, that particles of the preferred size were generated. The particles were dried in a fluid bed.

EXAMPLE 17

The same mixer as in example 4, i.e. Lödige FM 130 D, was loaded with 3 kg cellulose fiber and 12.0 kg activated carbon Picactif FGV (from the company Pica S.A., Levallois, Cedex, France) and sprayed with 20.0 kg 10% w/w gelatine Bloom 200 solution and finally with 4.5 kg water. The treatment time and rotation speeds of the mixer and the chopper was chosen in such manner, the particles of the preferred size were generated. The particles were dried in a fluid bed.

The utility of an immobilized enzyme product produced according to the invention appears from the following application experiment. An immobilized glucose isomerase product was produced generally as in example 12. The product contained 32.6% by weight of partially purified glucose isomerase and the crosslinking was performed as in example 12.

After the washing with 1% w/v sodium phosphate (pH=7.0) 27.6 g moist particles, corresponding to 10 g particle dry matter, were filled into a water jacketed column with a diameter of 1.5 cm. The column was maintained at 65° C. and a 45% w/w glucose syrup at pH 7.8 (adjusted with $Na_2CO_3$) was continuously pumped through the enzyme bed at a rate that would allow a 40–42% conversion of glucose to fructose. The initial activity was 538 IGIC/g prep. dry matter (the activity being calculated according to NOVO Analyseforskrift AF 147/6) and the activity halflife was determined to 450 hours. The outlet pH was 7.4–7.5.

For comparison it can be mentioned, that the widely used commercial immobilized glucose isomerase Sweetzyme ® has an activity of 225–300 IGIC/g and a similar activity half life, and in order to obtain an outlet pH of 7.4–7.5 with Sweetzyme at the same conditions as above indicated, i.e. 65° C. and 45% w/w glucose syrup, an inlet pH of 8.2 is necessary.

We claim:

1. An immobilized enzyme granule adapted for fixed bed or fluidized bed continuous enzymatic reactions comprising:
   (a) a continuous phase hydrophilic binder material,
   (b) a discontinuous phase particulate inert filler material of particle size less than 1/5 of the least dimension of the granule, said binder and filler being insoluble in the enzymatic reaction medium, and
   (c) enzyme immobilized to the binder material at the surfaces of said granule.

2. An immobilized enzyme granule adapted for employment in an aqueous medium comprising:
   (a) a continuous phase of hydrophilic binder material and a discontinuous phase of particulate inert filler material of particle size less than 1/5 of the least dimension of the granule, said binder and filler being water insoluble, and
   (b) enzyme crosslinked to the binder material at the surfaces of said granule.

3. The immobilized enzyme granule of claim 2 further comprising a protein binder material which is water insolubilized by reaction with glutaraldehyde, and an enzyme which is crosslinked to the binder material by reaction with glutaraldehyde.

4. The enzyme granule of claim 3 further comprising a gelatine binder and diatomaceous earth and cellulose fiber filler materials, and glucose isomerase as the enzyme.

5. Method for production of immobilized enzyme granules which comprises:
   (a) admixing a water soluble binder dissolved or dispersed in an aqueous medium, and water insoluble inert filler particles, thereafter forming carrier granules from said mixture, then rendering the binder water insoluble and immobilizing an enzyme to the binder material at the surfaces of the carrier granules each of said filler particles having a particle size less than 1/5 of the least dimension of the granule in which it is contained.

6. Method according to claim 5 further comprising shaping the mixture directly into granules by mechanical action.

7. Method according to claim 5 further comprising:
   (a) including a gellable agent dissolved in said aqueous medium, and
   (b) adding the aqueous mixture to a gelling medium for said agent so as to form granules, whereafter said binder is made water insoluble by reaction with a crosslinking agent followed by dissolving the gellable agent away from the granules.

8. Method according to claim 7 wherein the gellable agent is selected from the group consisting of alginate, carrageenan or chitosan.

9. Method according to claim 8 wherein the gelling medium is a solution containing a calcium, barium or potassium salt of polyphosphate or ferricyanide.

10. Method according to claim 5 wherein the binder comprises a protein.

11. Method according to claim 10 wherein the binder is insolubilized by being crosslinked through reaction with glutaraldehyde.

12. Method according to claim 5 wherein the amount of the discontinuous phase filler material forms between about 10 and about 98 weight %, in relation to the total weight of the immobilized enzyme granules.

13. Method according to claim 5 wherein the linear size of a single inert filler particle calculated as the diameter of a sphere with the same volume as the inert particle is less than 1/20 of the least dimension of the immobilized enzyme granule in which said filler particle is contained.

14. Method according to claim 5 wherein each immobilized enzyme granule is spherical or rounded, of average diameter between 0.1 and 5 mm.

15. Method according to claim 5 wherein the carrier granules are reacted with a solution containing both enzyme and crosslinking agent.

16. Method according to claim 15 further comprising introducing the carrier granules into a tower as a fluidized mass of carrier granules and then a solution containing the soluble enzyme and crosslinking agent is introduced thereinto, whereafter the granule mass is removed from the tower, whereby the enzyme crosslinks to the binder at the surface of each granule and the binder becomes water insoluble.

17. Method according to claim 5 further comprising introducing the formed carrier granules into a tower as a fluidized mass of carrier granules, introducing a solution of soluble enzyme into said fluidized mass whereafter the granule mass is removed from the tower and then treated with crosslinking agent, whereby the enzyme becomes crosslinked to the binder at the surface of each granule and the binder becomes water insoluble.

* * * * *